(12) United States Patent
Bahl et al.

(10) Patent No.: US 7,550,584 B2
(45) Date of Patent: Jun. 23, 2009

(54) METHODS OF PURIFYING BETA GLUCANS

(75) Inventors: Arun K. Bahl, Cornelius, NC (US); Sharon V. Vercellotti, Covington, LA (US); John R. Vercellotti, Covington, LA (US); Elias Klein, Louisville, KY (US)

(73) Assignee: Immudyne, Inc., Mt. Kisco, NY (US)

( * ) Notice: Subject to any disclaimer, the term of this patent is extended or adjusted under 35 U.S.C. 154(b) by 0 days.

(21) Appl. No.: 11/390,986

(22) Filed: Mar. 27, 2006

(65) Prior Publication Data

US 2006/0241079 A1 Oct. 26, 2006

Related U.S. Application Data

(63) Continuation of application No. 10/366,538, filed on Feb. 12, 2003, now Pat. No. 7,018,986.

(60) Provisional application No. 60/412,222, filed on Sep. 20, 2002.

(51) Int. Cl.
C07H 1/06 (2006.01)
C07H 1/08 (2006.01)

(52) U.S. Cl. ................ 536/127; 536/123.1; 536/124

(58) Field of Classification Search ............ 514/54, 514/75, 12, 231.5, 233.5, 381; 536/123.1, 536/123.12, 124; 435/69.1, 320.1; 424/130.1, 424/165.1, 169.1, 442
See application file for complete search history.

(56) References Cited

U.S. PATENT DOCUMENTS

| | | | |
|---|---|---|---|
| 4,138,479 A | 2/1979 | Truscheit et al. | 424/278.1 |
| 4,739,046 A | 4/1988 | Di Luzio | |
| 4,804,545 A * | 2/1989 | Goering et al. | 426/28 |
| 4,897,220 A | 1/1990 | Trieselt et al. | 510/360 |
| 5,223,491 A | 6/1993 | Donzis | 514/54 |
| 5,397,773 A | 3/1995 | Donzis | 514/54 |
| 5,401,727 A | 3/1995 | Rorstad et al. | 514/54 |
| 5,519,009 A | 5/1996 | Donzis | 514/54 |
| 5,576,015 A | 11/1996 | Donzis | 424/442 |
| 5,622,940 A | 4/1997 | Ostroff | |
| 5,702,719 A | 12/1997 | Donzis | 424/443 |
| 5,705,184 A | 1/1998 | Donzis | 424/442 |
| 6,117,850 A | 9/2000 | Patchen et al. | |
| 6,214,337 B1 | 4/2001 | Hayen et al. | 424/93.51 |
| 6,242,594 B1 * | 6/2001 | Kelly | 536/123.12 |
| 6,340,703 B1 | 1/2002 | Kelly | |
| 6,423,832 B1 | 7/2002 | Seljelid | 536/1.11 |
| 6,497,863 B1 | 12/2002 | Wachter et al. | 424/65 |
| 6,497,865 B1 | 12/2002 | Griesbach et al. | 424/70.1 |
| 6,500,410 B1 | 12/2002 | Griesbach et al. | 424/59 |
| 6,534,098 B2 | 3/2003 | Muhlbauer | |
| 6,858,214 B1 | 2/2005 | Kropf et al. | 424/401 |
| 6,875,754 B1 | 4/2005 | Griesbach et al. | 514/54 |
| 6,964,775 B1 | 11/2005 | Wachter et al. | 424/401 |

FOREIGN PATENT DOCUMENTS

WO WO 91/07091 5/1991

OTHER PUBLICATIONS

Babineau, Timothy J., et al., "Randomized Phase I/II Trial of a Macrophage-Specific Immunomodulator (PGG-Glucan) in High-Risk Surgical Patients," *Annals of Surgery*, vol. 220, No. 5, pp. 601-609, 1994.

Czop, Joyce K. et al., "Isolation and Characterization of β-Glucan Receptors on Human Mononuclear Phagocytes," *J. Exp. Med.*, vol. 173, pp. 1511-1520, Jun. 1991.

Sherwood, E.R., et al., "Glucan Stimulates Production of Antitumor Cytolytic/Cytostatic Factor(s) by Macrophages" *J. Biological Response Modifiers*, vol. 5, pp. 504-526, 1986.

Sherwood, E.R., et al., "Enhancement of Interleukin-1 and Interleukin-2 Production by Soluble Glucan," *Int. J. Immunopharmac.*, vol. 9, No. 3, pp. 261-267, 1987.

Williams, D.L., et al., "Immunopharmacologic Modification of Experimental Viral Diseases by Glucan," *J. Immun. and Immunopharmac.*, vol. 5, No. 2, pp. 78-82, 185.

Williams, D.L., et al., "Protective Effect of Glucan in Experimentally Induced Candidiasis," *J. of the Reticuloendothelial*, vol. 23, No. 6, pp. 479-490, Jun. 1978.

Ueno, Hiroiku, "Beta-1, 3-D-Glucan, its Immune Effect and its Clinical Use," *Japanese Journal Society Terminal Systemic Diseases*, vol. 6, pp. 151-154, 2000.

* cited by examiner

*Primary Examiner*—Patrick T Lewis
(74) *Attorney, Agent, or Firm*—DLA Piper LLP (US)

(57) ABSTRACT

The invention provides methods of using beta glucans to treat conditions associated with bone loss or low bone density as well as methods for promoting bone growth in situations where enhanced bone growth is desirable. In the invention methods beta glucans are administered so as to enhance the development of osteoblasts and the inhibition of the development and recruitment of osteoclasts. The inhibition of the recruitment and development of osteoclasts, coupled with the enhancement of osteoblast maturation by beta glucans leads to decreased bone resorption and increased bone formation, making beta glucans ideal agents for the treatment of osteoporosis and other bone resorption diseases.

24 Claims, 5 Drawing Sheets

Effect of Media Conditioned by Beta-G-treated Osteoblasts and Fibroblasts Upon Formation of TRAP+multinucleated Cells (MNC), Osteoclasts, *in vitro*

Ctrl - control
CT - calcitonin

Effect of Media Conditioned by Beta-G-treated Osteoblasts and Fibroblasts upon Formation of Osteoclastic Resorption Pits, *in Vitro*

Ctrl - control
CT - calcitonin

METHODS OF PURIFYING BETA GLUCANS

CROSS REFERENCE TO RELATED APPLICATION(S)

This application is a continuation application of U.S. application Ser. No. 10/366,538 filed Feb. 12, 2003, now issued as U.S. Pat. No. 7,018,986; which claims the benefit of priority under 35 USC § 119(e) to U.S. application Ser. No. 60/412,222, filed Sep. 20, 2002. The disclosure of each of the prior applications is considered part of and is incorporated by reference in the disclosure of this application.

BACKGROUND OF THE INVENTION

1. Field of the Invention

The present invention relates to methods for treating conditions associated with bone loss or low bone density, particularly osteoporosis.

2. Background Information

Bone is a specialized dynamic connective tissue that serves the following functions: (a) mechanical, support and site of muscle attachment for locomotion; (b) protective, for vital organs and bone marrow: (c) metabolic; as reserve of ions, especially calcium and phosphate, for the maintenance of serum homeostasis, which is essential for live. To carry out these functions efficiently bone must undergo continuous resorption and renewal, a process collectively known as remodelling. Thus, the mechanical and biological integrity of bone dependents on its continuous destruction (resorption) and continuous rebuilding (formation) at millions of microscopic sites. During adult life bone remodelling is crucial to eliminate and replace structurally damaged or aged bone with structurally new healthy bone. To maintain the proper bone mass resorption and formation are kept in perfect equilibrium. With age the equilibrium between bone resorption and formation becomes altered, often in favor of resorption, resulting in a reduction in bone mass, deterioration of bone architecture, decreased resistance to stress, bone fragility and susceptibility to fractures. The compendium of these symptoms is referred to osteoporosis.

Osteoporosis is a major health problem in Western society. And even though there are other diseases that result in reduction in bone mass, i.e. Paget's disease, osteoporosis is by far the most common and the disease that is the most costly in terms of health care. Since estrogen is a hormone that regulates bone metabolism directly and indirectly, the decrease in estrogen production in post-menopausal women and the decline with age in the production of androgen, which is enzymatically converted to estrogen in men, ) is responsible for the risk of osteoporosis, which is estimated to be 85% in women and 15% in men older than 45 years of age. In the United States it is estimated that 17 million post-menopausal women have lost 10% of their peak bone mass, 9.4 million have lost 25% and 5 million have suffered a fracture as a consequence of osteoporosis. Osteoporosis costs America's health care system more than $14 billion a year from spine and hip fractures, which are often the first indication of the disease if it is left undiagnosed.

Osteoporosis, a disease endemic in Western society, typically reflects an imbalance in skeletal turnover, such that bone resorption exceeds bone formation. Bone resorption is a specific function of osteoclasts, which are multinucleated, specialized bone cells formed by the fusion of mononuclear progenitors originating from the hemopoietic compartment, more precisely from the granulocyte-macrophage colony-forming unit (GM-CFU). The osteoclast is the principal cell type, to resorb bone, and together with the bone-forming cells, the osteoblasts, dictate bone mass, bone shape and bone structure. The increased activity and/or numbers of osteoclasts, relative to the activity and or numbers of bone-forming osteoblasts, dictates the development of osteoporosis and other diseases of bone loss.

Even though Paget's disease is not as common or as costly as osteoporosis—it affects 3% of the population over 40, and 10% of the population over 80 years of age—it is nonetheless a significant disease because aside from causing bone fractures it can lead to severe osteoarthritis and severe neurological disorders. Paget's disease is characterized by rapid bone turnover, resulting in the formation of woven bone a tissue type formed initially in the embryo and during growth and which is practically absence from the adult skeleton. Woven bone is marked by brittleness and therefore prone to fractures and bowing. Bones become enlarged and often interfere with blood flow and constrict nerves, resulting in many of the neurological symptoms associated with Paget's disease.

For a disease in which osteoclasts presumably resorb bone at abnormally high levels and osteoblasts form bone at normal levels, as in osteoporosis, the most reasonable therapeutic target would be the osteoclast: decreasing the number of osteoclasts and/or the resorption activity of the osteoclasts, should restore the equilibrium between bone resorption and formation. And, in fact, the treatments now available for osteoporosis are intended to suppress bone resorption.

Osteoclasts are derived from the monocyte-macrophage family. Upon stimulation of the CFU-GM with macrophage colony stimulating factor (M-CSF) form promonocytes which are immature nonadherent progenitors of mononuclear phagocytes and osteoclasts. The promonocytes, may proliferate and differentiate along the macrophage pathway, eventually forming a tissue macrophage, or may differentiate along the osteoclast pathway, depending on the cytokines to which they become exposed. For example, the receptor activator NF-κB ligand (RANKL) (Simonet W S, Lacey D L, Dunstan R, Kelley M, Chang M-S, Luethi R et al 1997 Osteoprotegerin, a novel secreted protein involved in the regulation of bone density. Cell 89:309-319) a cytokine expressed on the membrane surface of osteoblasts influences promonocytes to differentiate into osteoclasts rather than macrophages, while treatment with M-CSF drives the promonocyte to develop into macrophages. Since M-CSF and other cytokines i.e., interleukin-1 or TNF-α, that support expression of RANKL are products of macrophages it may be assumed that immunomodulating substances, which alter the expression of, these cytokines and growth factors, may affect not only macrophages but also osteoclasts.

It has long been known that beta glucans, and particularly the beta glucans from yeast, activate macrophages and have profound effects on the synthesis and levels of many cytokines, which in turn are responsible for modulating the function of many other cells. (Stoy, Y. "Macrophage biology and pathobiology in the evolution of immune responses: a functional analysis," *Pathobiology*, 69:179-211, 2001; Underhill D M, Ozinshy, A. "Phagocytosis of microbes: complexity in action," *Annu Rev Immunol.* 20:825-52, 2002; Purohit A, Newman S P, Reed M J. "The role of cytokines in regulating estrogen synthesis: implications for the etiology of breast cancer," *Breast Cancer Res* 4:65-69, 2002; Ismail N, Olano J P, Feng H M, Walker D H. "Current status of immune mechanisms of killing intracellular organisms" *FEMS Microbiol Lett* 207:111-120, 2002; Hubel K, Dale D C, Liles W C. "Therapeutic use of cytokines to modulate phagocyte function for the treatment of infectious diseases: current status of granulocyte colony stimulating factor, granulocyte-macrophage stimulating factor, macrophage colony stimulating factor and interferon gamma" *J Inf Dis* 185: 1490-1501, 2002.).

Even though there are a number of therapeutic modalities for osteoporosis, which include bisphosphonates (Fleisch H, "Development of biphosphonates," *Breast Cancer Res.* 4:30-34, 2002), estrogen (Spencer, C P, Stevenson. J C "Oestrogen and anti-oestrogen for the prevention and treatment of osteoporosis." In Osteoporosis: Diagnosis and Management, Martin Muniz, England, 1998, pp 111-123), or "Selective Estrogen Receptor Modulators," (SERMS) most of these have significant undesirable side-effects.

Glucans are polysaccharides consisting of glucose subunits. β-(1,6) branched β-(1,3) glucan is a naturally occurring class of polysaccharides that can be extracted from Baker's yeast and other yeast species, mushrooms, plants and some bacterial, lichen and algal species (reviewed in Chemistry and Biology of (1→3)-β-Glucans, B. A. Stone and A. E. Clarke, 1992, La Trobe University Press, Australia). β-(1,6) branched (1,3) glucans have been shown to have immune enhancing and cholesterol-lowering capabilities. Yeast synthesizes at least three different types of beta glucans, a linear β-1,3-D-glucans, a linear β-1,6-D-glucan and a β-(1,6) branched β-(1,3) glucan. However, linear β-1,3-D and linear β-1,6-D-glucans do not activate or only marginally activate macrophages, NK cells or neutrophils.

As a class of polysaccharides, β-(1,6) branched β-(1,3) glucans are composed of a main chain of glucose subunits linked together in and branches linked to the main chain by a (1→6) β glycosidic linkage. Yeast β-(1,6) branched β-(1,3) glucan is composed of mostly of a main chain of glucose units linked by (1→3) beta glycosidic linkages (90% or more) with a variable number of relatively short side chains linked by β-(1→6) glycosidic linkages (10% or less); the chemical name for this glucan is poly-(1,3)-β-D-glucopyranosyl-(1,6)-β-D-glucopyranose. There are several different types of beta glucans, which vary in backbone composition, branching, type of monomers or substituents, resulting in polysaccharides that have very different physical and biological properties (Metz, Ebert, and Weicher, Chromatographia 4:345,1970; Manners et al., The structure of β-(1-3) D-glucan from yeast cell walls. Biochem. J.135:19, 1973; U.S. Pat. No. 5,223,491).

Whereas all the β-1,3/1,6-D-glucans have been shown to activate the immune system of vertebrate as well as invertebrate organisms, the yeast-derived β-1,3/1,6-D-glucan is a most powerful activator of macrophages, NK cells, and neutrophils. Beta glucan from yeast activates the immune system by binding to a specific receptor on the cell membrane of macrophages (Czop and Kay, Isolation and characterization of β-glucan receptors on human mononuclear phagocytes. J. Exp. Med. 173:1511-1520, 1991). The activated macrophages increase their phagocytic and bactericidal activities as well as the production of a wide range of cytokines (Burgaletta, C and Golde, D W, in Immune Modulation and control of neoplasia by adjuvant Therapy (Chirigos, M. A., ed), pp 195-200. Raven Press, NY, 1978; Sherwood et al., "Glucan stimulates production of antitumor cytolytic/cytostatic factors by macrophages," *J. Biol Resp. Mod.,* 6:358-381; Sherwood, et al., "Enhancement of interleukins 1, and interleukins 2 production by soluble glucan"; Browder et al., "Beneficial effects of enhanced macrophage function in the trauma patient," *Ann. Surg.* 211:605-613). Enhanced function of macrophages, as well NK cells, appear responsible for a number of beneficial effects of yeast beta glucan, such as increased resistance of the host to infection by bacteria, viruses, fungi and protozoan parasites (Williams et al., "Protective effect of glucan in experimentally induced candidiasis," *J. Reticuloendot. Soc.* 23:479-490, 1978; Williams and DiLuzio. "Immunopharmacological modification of experimental viral diseases by glucan," EOS JK *Immunol Immunopharmacol* 5:78-82, 1985; Babineau et al. "A phase II multicenter, double blind, randomized, placebo-controlled study of three dosages of an immunomodulator (PCG-glucan) in high risk surgical patients," *Arch. Surg.,* 129:601-609., 1994). In addition, the enhanced function of macrophages and NK cells appears to increase the host defenses against malignant tumors (Mansell et al. "Macrophage mediated destruction of human malignant cells in vivo," *J Natl Canc. Inst.* 54:571-576, 1975; Williams et al. "Chemoimmunotherapy of experimental hepatic metastasis," *Hepatology,* 7:1296-1304, 1985; Ueno. "Beta-1,3-D-glucan, its immune effect and its clinical use," *Jap. J Soc. Terminal Systemic Dis.* 6:151-154, 2000).

Beta-1,3/1,6-D-glucan isolated from baker's or brewer's yeast (*Saccharomyces cerevisiae* strain) as well other yeasts, is insoluble, and furthermore the variability in the number of beta-(1,6) side chains makes it extremely difficult if not impossible to determine whether the beta-1,3/1,6-D-glucan is the branched beta-1,3/1,6-D-glucan or a mixture of beta-1,3-D-glucan plus beta-1,6-D-glucan, or a mixture of all three beta glucans. Yeast makes all three types of beta glucans. Since only the branched beta-1,3/1,6-D-glucan activates macrophages, it would be desirable to have pure beta-1,3/1,6-D-glucan; in addition, insoluble beta-1,3/1,6-D-glucan is difficult to formulate for parenteral or topical administration. It would be desirable to have a beta glucan that could be easily characterized, and which could be easily formulated for topical and parenteral administration. In addition, it would be of benefit for formulation purposes to have a lower molecular weight beta glucan that retains biological activity. A low molecular weight, soluble beta-1,3/1,6-D-glucan used topically would also be able to penetrate faster and, used parenterally, would very likely reach tissue macrophages faster, resulting in an earlier activation.

To date the soluble beta glucans that have been available are all of the high molecular weight variety, and for the major part these glucans were made soluble by chemical modifications or solubilized by sequential treatments with alkali/acid/alkali. A number of soluble glucans have been obtained by derivatization of the natural, insoluble beta-1,3/1,6-D-glucan compound, such as phosphorylation (U.S. Pat. Nos.: 4,739, 046; 4,761,402), sulfation, amination (U.S. Pat. No.: 4,707, 471) or methylation. A beta-1,3/1,6-D-glucan solubilized by sequential treatment with alkali/acid/alkali of insoluble beta-1,3/1,6-D-glucan (U.S. Pat. No. 5,849,720) has been shown to be effective in humans to control infections in surgical patients (Babineau et al. A phase II multicenter, double blind, randomized, placebo-controlled study of three dosages of an immunomodulator (PCG-glucan) in high-risk surgical patients (*Arch. Surg.,* 129:601-609, 1994).

There is therefore a need for therapies to inhibit or prevent bone loss that have less or no side effects and offer more natural biological mechanisms.

SUMMARY OF THE INVENTION

The present invention is predicated on the surprising finding that beta glucans are able to suppress osteoclast development and may enhance the development of osteoblasts.

In one embodiment, the invention is directed to methods of treating conditions in which there is a loss or decrease in bone mass in mammals by administering a beta glucan, or a pharmaceutically acceptable salt thereof.

In particular this invention is directed to such methods wherein the condition is osteoporosis, Paget's disease, a bone defect, childhood idiopathic bone loss, alveolar bone loss, or bone fracture.

In another embodiment, the invention provides methods for promoting bone growth in a mammal in need thereof comprising administering to said mammal an effective amount of beta glucan, or a pharmaceutically acceptable salt of the beta glucan, so as to promote bone formation.

DETAILED DESCRIPTION OF THE INVENTION

The present invention provides methods and compositions for the treatment of osteoporosis, Paget's disease and other conditions which present with low bone mass or result in the loss of bone, particularly when the loss of such bone results from increased numbers of osteoclasts and/or increased bone resorbing activity of osteoclasts.

In the invention methods for treating a condition associated with low bone mass in a mammal an effective amount of beta glucan, or a pharmaceutically acceptable salt of the beta glucan, is administered so as to inhibit bone resorption and/or increase bone formation.

Methods for treating "secondary osteoporosis" are also included within the methods of this invention. "Secondary osteoporosis" includes glucocorticoid-induced osteoporosis, hyperthyroidism-induced osteoporosis, immobilization-induced osteoporosis, heparin-induced osteoporosis and immunosuppressive-induced osteoporosis in a vertebrate, e.g., a mammal (including a human being). These methods are carried out by administering to said vertebrate, e.g., mammal, a "secondary osteoporosis" treating amount of a beta glucan or a pharmaceutically acceptable salt thereof.

Figure 2:
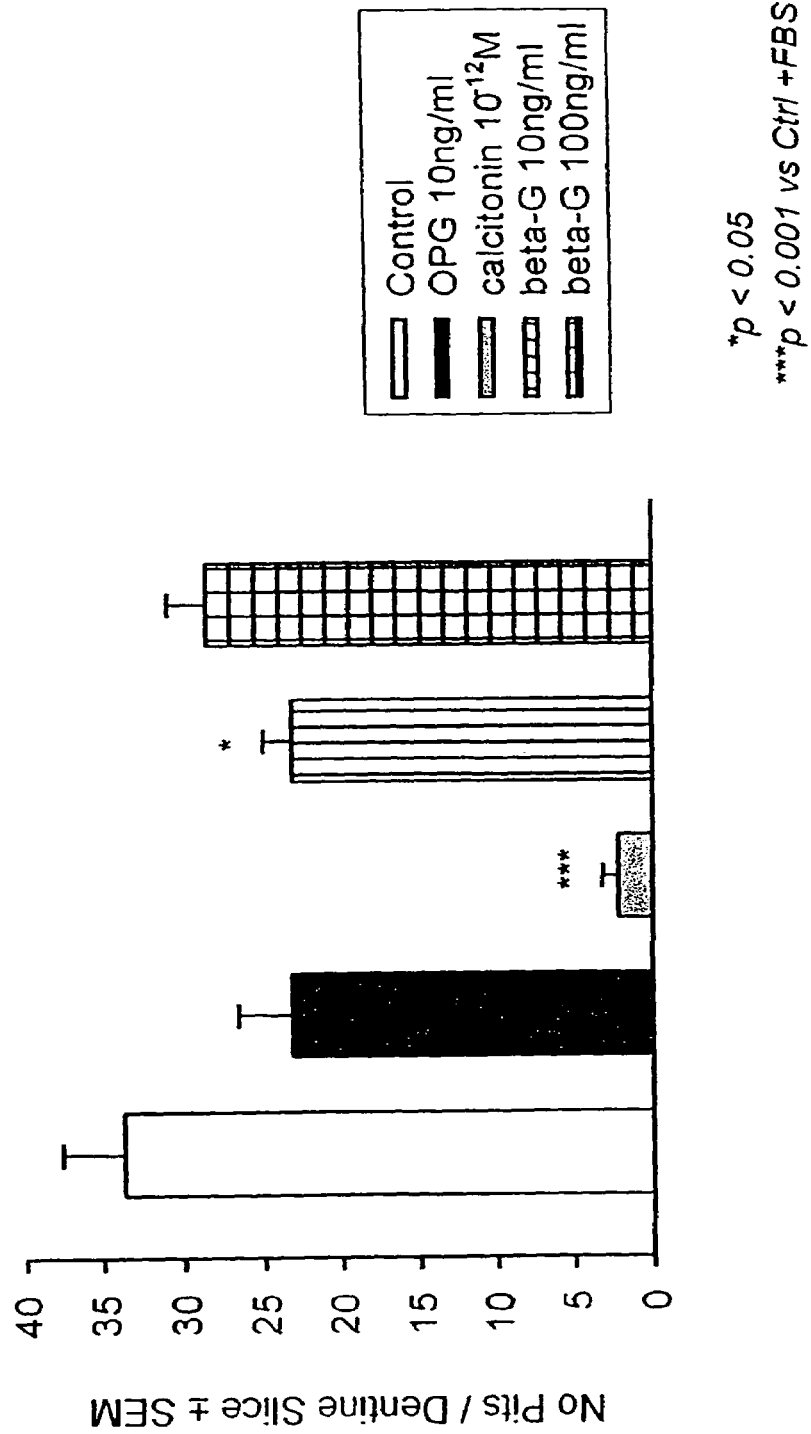
FIG. 2 is a graph showing inhibition of osteoclast-mediated resorption in vitro by osteoprotegerin (commercial product) and beta glucan.

The inhibition of osteoclast activity in the invention methods can be the result of an inhibitory activity of the resorption mechanisms of the osteoclasts or can be the result of an inhibition of the number of osteoclasts recruited from precursor cells, or a combination of both. In an analysis of osteoclast recruitment, extremely low concentrations of beta glucan decreases the number of osteoclasts formed (FIG. 2). At concentrations as low as 100 pg there is a decrease of 30% and at concentrations of 1 ng and 10 ng there is an inhibition of approximately 50%. Increasing the concentration of beta glucan does not increase the inhibition of osteoclast formation rather the effect diminishes. This observation is consistent with the fact that beta glucan has its effect via a receptor and that high concentrations may lead to receptor down-regulation.

In osteoporosis, which affects mostly older individuals and particularly post-menopausal women, combined with increased bone resorption there is a slow-down in bone formation by osteoblasts, which occurs normally due to the aging process. As used in the invention methods of treatment, beta glucan enhances osteoblast formation, thus also increasing bone formation.

In another embodiment, the invention provides methods for promoting bone growth in a mammal in need thereof by administering thereto an effective amount of a beta glucan, or a pharmaceutically effective amount thereof. Conditions wherein promotion of bone growth is beneficial include strengthening a bone graft, inducing vertebral synostosis, enhancing long bone extension, enhancing bone healing following facial reconstruction, maxillary reconstruction and/or mandibular reconstruction in a vertebrate, e.g., a mammal (including a human being), and the like.

Figure 1:
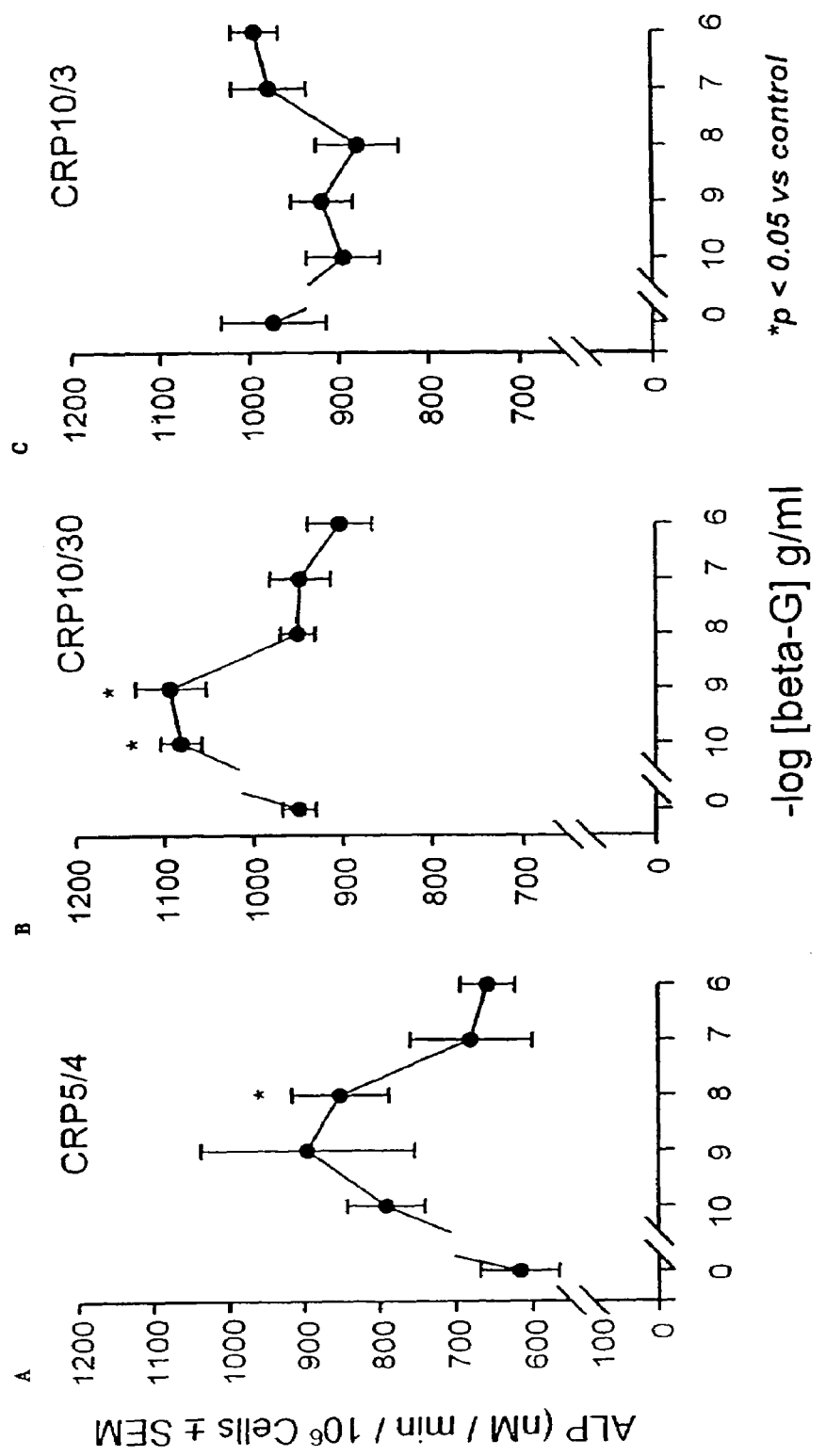
FIGS. 1 A-C is a series of graphs showing the effect of beta glucan upon alkaline phosphatase of rat osteoblasts of different maturation.

An "effective amount" of beta glucan for use in treating a condition associated with bone loss or in a condition wherein promotion of bone growth is beneficial is an amount sufficient to inhibit bone loss and/or increase bone formation or to inhibit osteoclast activity. Those of skill in the art will consider such factors as the mammal's age, level of activity, hormone balance, general health in determining the effective amount, which is tailored to the subject, for example by beginning with a low dosage and titrating the dosage to determine the effective amount. By the studies described herein it has been discovered that increasing the concentration of beta glucan does not necessarily increase the inhibition of osteoclast activity, and may actually reduced inhibition of osteoclast activity (FIG. 1). At 100 pg the effect is similar to the effect obtained with bisphosphonates, which in various forms are used as drugs to control osteoporosis.

The phrase "condition(s) associated with low bone mass" refers to a condition where the level of bone mass is below the age specific normal as defined in standards by the World Health Organization "Assessment of Fracture Risk and its Application to Screening for Postmenopausal Osteoporosis (1994). Report of a World Health Organization Study Group. World Health Organization Technical Series 843". Included in "condition(s) associated with low bone mass" are primary and secondary osteoporosis, as described above. Also included is periodontal disease, alveolar bone loss, post-osteotomy and childhood idiopathic bone loss. The phrase "condition(s) associated with low bone mass" also includes long term complications of osteoporosis such as curvature of the spine, loss of height and prosthetic surgery.

The phrase "condition(s) which present with low bone mass" also refers to a vertebrate, e.g., a mammal known to have a significantly higher than average chance of developing such diseases as are described above including osteoporosis (e.g., post-menopausal women, men over the age of 50). Other bone mass augmenting or enhancing uses include bone restoration, increasing the bone fracture healing rate, replacing bone graft surgery entirely, enhancing the rate of successful bone grafts, bone healing following facial reconstruction or maxillary reconstruction or mandibular reconstruction, prosthetic ingrowth, vertebral synostosis or long bone extension. Those skilled in the art will recognize that the term bone mass actually refers to bone mass per unit area, which is sometimes (although not strictly correctly) referred to as bone mineral density.

The methods of this invention may also be used in conjunction with orthopedic devices such as spinal fusion cages, spinal fusion hardware, internal and external bone fixation devices, screws and pins.

The term "treating", "treat" or "treatment" as used herein includes preventative (e.g., prophylactic), palliative and curative treatment. The methods of this invention result in bone formation resulting in decreased fracture rates. This invention makes a significant contribution to the art by providing methods that increase bone formation resulting in prevention, retardation, and/or regression of osteoporosis and related bone disorders.

By "pharmaceutically acceptable" it is meant the carrier, vehicle, diluent, excipients, and/or salt must be compatible with the other ingredients of the formulation, and not deleterious to the recipient thereof by the route administered.

The expression "pharmaceutically acceptable salt" refers to such nontoxic anionic salts containing anions such as (but not limited to) chloride, bromide, iodide, sulfate, bisulfate, phosphate, acetate, maleate, fumarate, oxalate, lactate, tartrate, citrate, gluconate, methanesulfonate and 4-toluene-sulfonate, and the like, that can be injected into the body.

Beta glucan is a naturally occurring class of polysaccharides that can be extracted from Baker's yeast and other yeast species, mushrooms, plants and some bacterial, lichen and algal species (reviewed in Chemistry and Biology of (1→3)-β-Glucans, B. A. Stone and A. E. Clarke, 1992, La Trobe University Press, Australia). β-(1,6) branched (1,3) glucans have been shown to have immune enhancing and cholesterol-lowering capabilities. Yeast synthesizes at least three different types of beta glucans, a linear β-1,3-D-glucans, a linear β-1,6-D-glucan and a β-(1,6) branched β-(1,3) glucan. However, linear β-1,3-D-glucans and linear β-1,6-D-glucans do not activate or only marginally activate macrophages, NK cells or neutrophils. In one embodiment of the invention methods, the beta glucan retains the biological activity of macrophage activation, such as a water soluble 1→6 branched 1→3 beta glucan. In another embodiment, the beta glucan contains 2 to 20% beta 1→6 branching and/or has a molecular weight of about 1500 to about 100,000.

Figure 3:
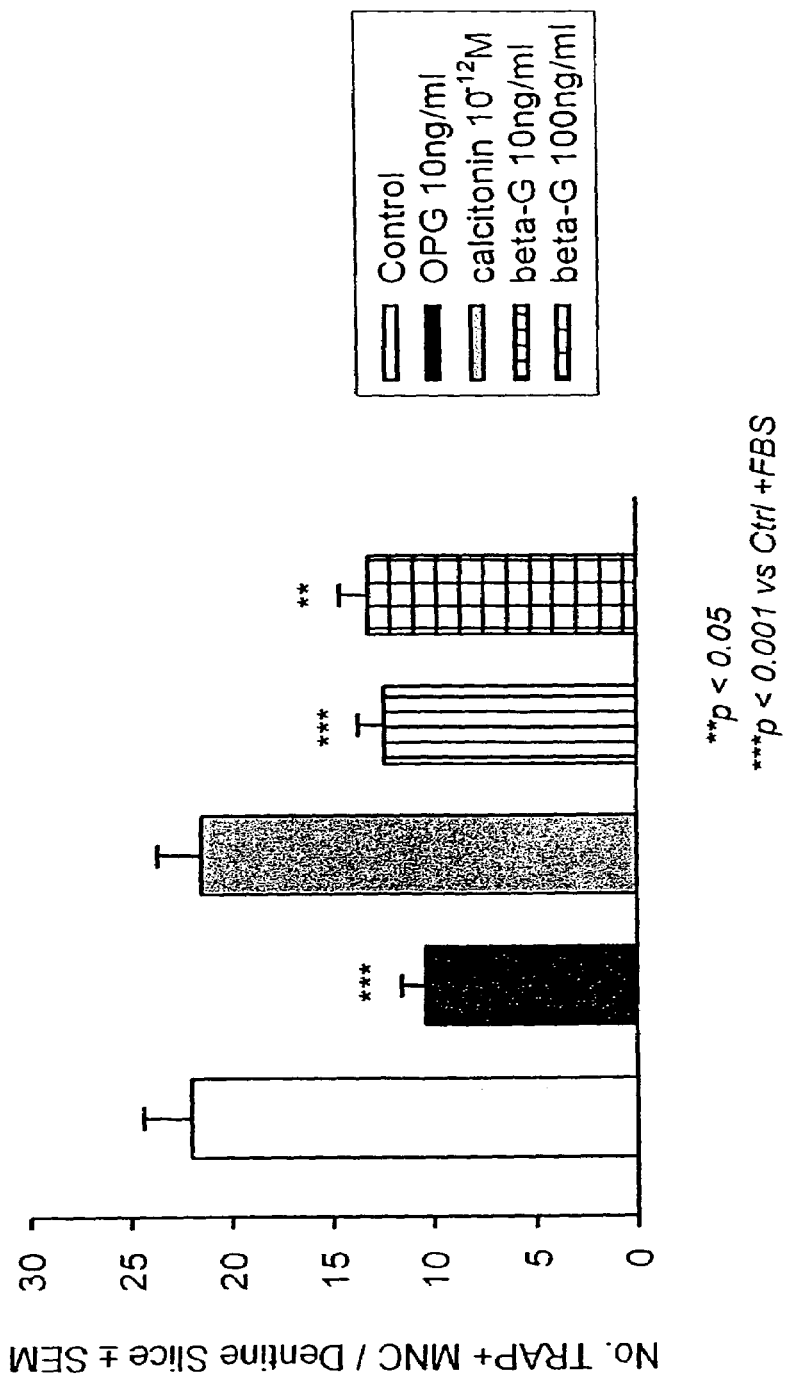
FIG. 3 is a graph showing inhibition of osteoclast formation by osteoprotegerin (commercial product) and beta glucan.
Figure 4:
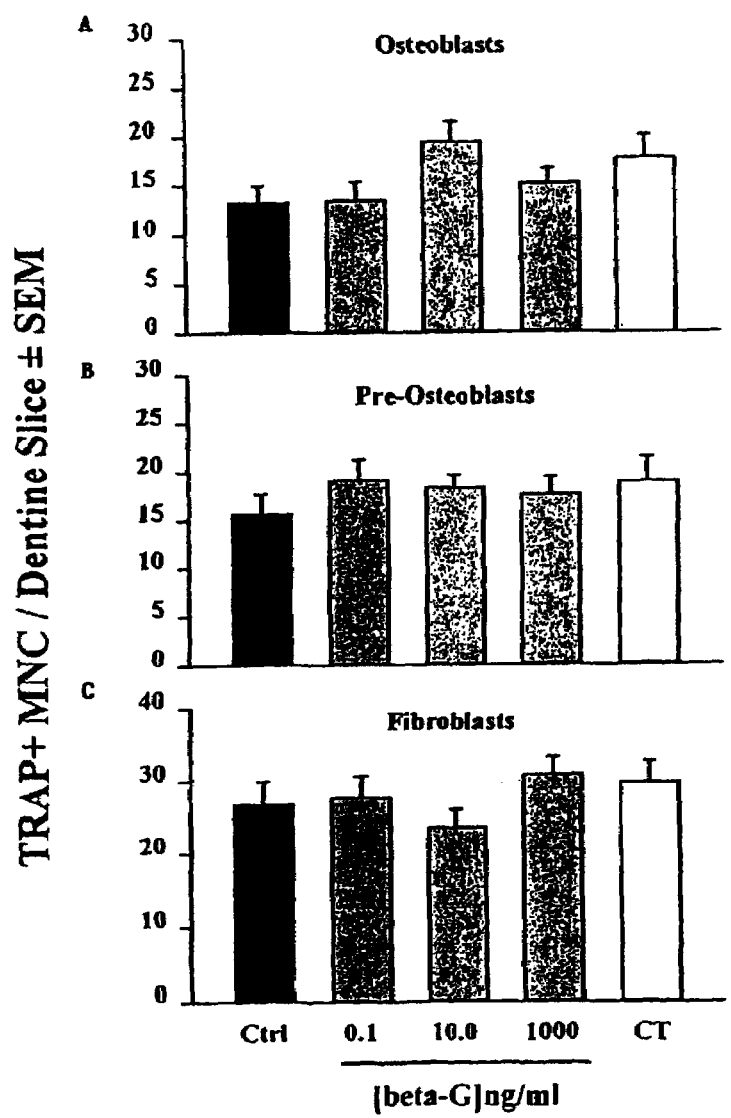
FIGS. 4 A-C is a series of graphs showing the effect of media conditioned by beta glucan-treated osteoblasts and fibroblasts on formation of TRAP$^+$ multinucleated cells (MNC) and osteoclasts in vitro.

For example, a yeast beta-1,3/1,6-D-glucan suitable for use in practice of the invention methods can be obtained from the yeast $Saccharomyces$ $cerevisiae$. Such a beta glucan can be derived from a yeast cell wall preparation containing mostly yeast beta-1,3/1,6-D-glucan or from purified yeast beta-1,3/1,6-D-glucan by enzymatic degradation with a beta endoglucanase as described herein. Other beta glucans also have anti-resorptive activity and are suitable for use in practice of the invention methods. For example, in FIG. 3 it is evident that the insoluble yeast beta glucan (Nayad), a beta glucan isolated from the mushroom $Blazei$ $agaricus$ also inhibits pit formation by osteoclasts. FIG. 4 shows that all beta glucans examined (yeast soluble and insoluble (Nayad), beta glucan from $Blazei$ $agaricus,$ $Yunzhi$ beta glucan and even Zymosan, which is a hot alcoholic extract of yeast with immuno-modulating activity, due to the beta glucan in Zymosan) are capable of inhibiting the formation of osteoclasts.

The utility of the beta glucans used in the methods of the present invention as medical agents in the treatment of conditions associated with low bone mass (e.g., osteoporosis) in vertebrates, e.g., mammals (especially humans and particularly female humans) is demonstrated by the activity in bone resorption assays as are known in the art and as described herein. Such assays also provide a means whereby the activities of beta glucans can be compared to each other and with the activities of other known compounds and compositions useful for treating such conditions. The results of these comparisons are useful for determining dosage levels in vertebrates, e.g., mammals, including humans, for the treatment of such diseases.

The preferred route of administration of the beta glucans as used in the invention methods is systemic administration, e.g., orally, subcutaneously, intramuscularly or via aerosol. For example, formulations or compositions containing a hydrolyzed beta glucan can be injected parenterally, for example by injection into the peripheral circulation.

In another embodiment, the invention provides methods for promoting bone growth in a mammal in need thereof by administering thereto an effective amount of a beta glucan, or a pharmaceutically effective amount thereof. Conditions wherein promotion of bone growth is beneficial include strengthening a bone graft, inducing vertebral synostosis, enhancing long bone extension, enhancing bone healing following facial reconstruction, maxillary reconstruction and/or mandibular reconstruction in a vertebrate, e.g., a mammal (including a human being), and the like.

An "effective amount" of beta glucan for use in treating a condition associated with bone loss or in a condition wherein promotion of bone growth is beneficial is an amount sufficient to inhibit bone loss and/or increase bone formation or to inhibit osteoclast activity. Those of skill in the art will consider such factors as the mammal's age, level of activity, hormone balance, general health in determining the effective amount, which is tailored to the subject, for example by beginning with a low dosage and titrating the dosage to determine the effective amount. By the studies described herein it has been discovered that increasing the concentration of beta glucan does not necessarily increase the inhibition of osteoclast activity, and may actually reduced inhibition of osteoclast activity (FIG. 1). At 100 pg the effect is similar to the effect obtained with a bisphosphonate, which in various forms are used as drugs to control osteoporosis.

The beta glucan used in the invention methods can be contained in a formulation comprising a carrier suitable as is known in the art to the desired mode of administration, i.e., injection into the peripheral circulation. The composition may also include one or more compounds known in the art to be beneficial to bone formation, such as calcium, fluoride, magnesium, boron, or a combination thereof.

Soluble beta-1,3/1,6-D-glucan for use in the invention methods of treating conditions in which there is a loss or decrease in bone mass in mammals or the need to promote bone formation can be produced and manufactured from yeast or other microorganisms containing beta-1,3/1,6-D-glucan using the following steps:

a. Yeast cells or cell walls are treated with a base at high temperature to solubilize alkali soluble components of the cell
b. After washing with water, the residue is treated with an acid at high temperature Alternatively, $a_1$. Yeast cell walls are treated with an acid
$b_1$. After washing water, the residue is treated with sodium hypochlorite
c. After washing with water, the residue is hydrolyzed with a beta glucanase at a specific temperature
d. The mixture is centrifuged and the residue discarded
e. The supernatant is ultrafiltered through a membrane with a nominal weight cut-off of 100,000 daltons
f. The effluent is ultrafiltered through a membrane with a nominal molecular weight cut-off of 1000 daltons
g. The retentate is concentrated and suspended in 100% ethanol
h. The precipitate is washed with ethanol and dried.

i. If so desired, this material can further be purified and fractionated by ultrafiltration through a series of membranes with different molecular weight cut-offs or by chromatography.

The process of manufacture detailed here provides a soluble beta-1,3/1,6-D-glucan of low molecular weight, which retains the ability to activate macrophages. The manufacture of the soluble beta-1,3/1,6-D-glucan is achieved by first treating the organism containing beta-1,3/1,6-D-glucan (e.g., yeast cells or yeast cell walls) with alkali and acid solutions to remove non-beta glucan components, which makes the beta glucan available to the action of the enzyme. This treatment is then followed by enzymatic hydrolysis and purification of the solubilized beta-1,3/1,6-D-glucan.

Whole yeast cells or cell walls (Saccharomyces cerevisiae) are suspended in an alkaline solution and heated. The alkaline solution can be an alkali-metal or an alkali-earth metal hydroxide, such as sodium hydroxide or potassium hydroxide having a concentration from about 0.05 N to 10 N. This step is conducted at a temperature of 4° C. to 150° C., but preferably at 80° C. This step can be conducted at normal atmospheric pressure or at an elevated pressure, but preferably at 15 psi and 121° C. The treatment time may vary from about 10 minutes to 48 hours depending on the strength of the alkali solution and the temperature and the type of organism. Once the alkali treatment is complete, the residue is separated from the solution by an appropriate method, such as filtration or centrifugation. This alkali can be repeated one time or more.

The residue is washed with water one or more times and then extracted with an acid, such as hydrochloric acid, formic acid, acetic acid or other. An acid solution of pH 1 to 5 is usually sufficient at a temperature 4° C. to 150° C., for 15 minutes to 48 hours. The preferred conditions are extraction with acid is acetic acid at a concentration of 3% and at a temperature of 85° C. for 45 minutes. The insoluble material is separated from the solution by an appropriate procedure. The residue is then washed one or more time with water and again separated by an appropriate method.

Yeast cell walls can first be treated with an acid, such as hydrochloric acid, formic acid, acetic acid or other. An acid solution of pH 1 to 5 is usually sufficient at a temperature 4° C. to 150° C., for 15 minutes to 48 hours. The preferred conditions are extraction with acid is acetic acid at a concentration of 4% at a temperature of 85° C. for 45 minutes. The insoluble material is separated from the solution by an appropriate procedure. The residue is then washed one or more times with water and again separated by an appropriate method.

The residue is then extracted with sodium hypochlorite at a concentration from 15 to 75% at a temperature ranging from 4° C. to 150° C., for 15 minutes to 48 hours. The residue is then washed with water one or more times.

The residue is the treated with an enzyme that has endo-glucanase activity at a temperature from 10° C. to 80° C., for 15 minutes to 48 hours depending on the temperature, liquid to solids ratio, and concentration of the enzyme. The soluble enzyme digest is separated from the undigested material by an appropriate technique, such as centrifugation, filtration, etc. The soluble digested material can then be fractionated into discrete fractions by ultrafiltration, chromatography, sedimentation, electrofocusing, etc.

The invention will now be illustrated by the following non-limiting examples.

EXAMPLE 1

Prepartation of Soluble Beta-1,3/1,6-D-Glucan from Yeast Cells

*Saccharomyces cerevisiae* cells are added to 10 volumes of 1.5 N NaOH with stirring. The mixture is then heated at 60° C. for 30 minutes. The heated mixture is then autoclaved for 15 minutes at 15 psi and 121° C. The mixture is cooled and the supernatant is separated from the residue by centrifugation. The residue is washed with 10 volumes of water for 15 minutes with stirring. After separating the supernatant by centrifugation, 10 volumes of 3% acetic acid at 37° C. are added to the residue and the mixture is heated at 85° C. for 45 minutes with stirring. The mixture is cooled and the supernatant is separated from the residue by centrifugation. The residue, which is impure beta-1,3/1,6-D-glucan, is washed with water for 15 minutes with stirring.

The impure beta-1,3/1,6-D-glucan is suspended in 3 volumes of water and added to another 20-25 volumes of water at 40° C. To this mixture are added 100 ml of Viscozyme L beta-1,3-glucanase purchased from Novo Nardisk, Farnkliton, N.C. This mixture is stirred and heated to 80° C. The slurry is then pumped through a fiber filter unit equipped with a filter with a molecular weight cut-off of 100,000 daltons. The retentate is recycled continuously over a 10 hr period, always maintaing the volume constant in the reaction vessel by adding water at 80° C. The ultrafiltrate is collected continuously over the 10 hr period. Reducing sugar is checked in the ultrafiltrate every one liter collected. The ultrafiltrate is pumped through the inside of hollow fibers with a molecular weigh cut-off of 1500, to dialyze of salt and low molecular weight pigments or sugars. Dialysis is carried out by pumping water through the outer shell of the hollow fiber unit at 800 ml/min. After 10 hours 14.5 liters of ultrafiltrate is collected. The ultrafiltrate is concentrated by reverse osmosis followed by concentration with a rotary evaporator. The beta-1,3/1,6-D-glucan is precipitated from concentrated in the cold overnight ultrafiltrate with 10 volumes of 95% ethanol. The precipitate is collected, washed with 95% ethanol and dried.

The dried precipitate can be further purified by chromatography (e.g. affinity, gel permeation, chromatofocusing, etc.)., or filtration with membranes of varying molecular weight cut-offs ( Vercellotti et al. "Chemistry of membrane separation processes in sugar industry applications," *Zuckerindustrie* 123:736, 1998).

FIG. 1 shows an HPLC gel permeation chromatograph of the alcohol precipitate.

Table 1 shows a typical composition of the alcohol precipitated water soluble beta-1,3/1,6-D-glucan.

TABLE 1

| Component | % |
|---|---|
| Total carbohydrate | 98 |
| Glucose | 72 |
| Mannose | 16 |
| Protein | 4 |
| Lipid | 0 |
| Ash | 2 |

Table 2 shows some physical characteristics of the alcohol precipitated water soluble beta-1,3/1,6-D-glucan.

TABLE 2

| | |
|---|---|
| Molecular Weight (Gel Permeation Chromatography) | 12,000-60,000 daltons |
| Solubility | 2.5 gm/ml |
| Color in water | Light beige |
| Absorption at 280 nm ($E^{1\%}$) | 2632 |
| pH of a 1% solution in water | 7.0 |
| β (1→3) bonds (%) | 83 |
| β (1→6) bonds (%) | 17 |
| α (1→4) bonds (%) | None |

Table 3 shows the activation of macrophages in vitro (increase in interleukin 1 and $H_2O_2$ production) by the soluble alcohol precipitated water soluble beta-1,3/1,6-D-glucan.

TABLE 3

| | IL-1[1] | Bb[2] (ng) |
|---|---|---|
| Control | 0.05 | 4.2 |
| Zymosan[3] | ND | 13 |
| WS100[3] | 0.23 | 36 |

[1]Stimulation Index
[2]Bb released indicates activation of the Alternative Complement Pathway
[3]Data is for 1 mg/ml used in the assays

EXAMPLE 2

In Vintro Bio-Assay to Assess the Effect of Beta-Glucan on Osteoclast Formation and Activity by Beta Glucan To determine the effect of beta glucan on osteoclast-mediated resorption a modification of the bioassay described by Collin et al was used (Collin P, Guenther H L, Fleisch H Constitutive expression of osteoclast-stimulating activity by normal clonal osteoblast-like cells: effects of parathyroid hormone and 1,25-dihydroxy-vitamin $D_3$. Endocrinology 131: 1181-1187, 1992). The principle of the bioassay is based on cultivating freshly isolated disaggregated osteoclasts on elephant dentin (ivory) surfaces and measure the formation of resorption lacunae excavated by actively resorbing osteoclasts.

EXAMPLE 3

Isolation and Culture of Osteoclasts

Osteoclasts were isolated from femurs of 1-day-old rats (Wistar) as outlined elsewhere (Collin P et al. 1992, see above). Briefly, after killing the animals, femurs were dissected freed of adherent soft tissue and subsequently cut across the epiphysis to remove the marrow. The femurs were then placed in a dish containing 1 ml MEM supplemented with 0.5% gentamicin. Osteoclasts were gently released from the femurs using in succession calibrated dental needles of size 20 and 30. Resulting osteoclast suspension was then brought to a volume of 8 ml with MEM. and 500 μl of the cell preparation were added to eight ivory slices kept individually in plastic wells (2.0×1.0 cm). After 25-min incubation at 37 C and 5% $CO_2$/air, nonadherent cells were removed by lateral agitation. Next, eight slices for control and 8 for each treated group were individually transferred into single wells of a 24-well plastic tissue culture plate to which 500 μl of either control or test media were added. The cultures were carried out in MEM at 37 C and 5% $CO_2$/air. After 24 h, cells cultured on ivory slices were washed with 0.5 ml PBS. Thereafter the cells were fixed and subsequently stained for TRAP according to instructions of the manufacturer (Sigma). Individual slices were then examined for TRAP+ multinucleated cells (MNC) containing at least three nuclei per cell. Following enumeration the TRAP+ MNC were removed by ultrasound in 70% propanol. Thereafter the dentine slices were washed, air-dried and sputter-coated with gold (SCD 004 Coater, Balzers, Liechtenstein). The number of resorption pits on each ivory slice was scored with a light microscope equipped with a tangential light, at a magnification×200. A pit was defined as a depression in the ivory surface with a continuous rim and an area of at least 250 $\mu m^2$. Pit areas were calculated from pit images that were captured by a camera attached to the reflected light microscope with the aid of image analysis software (NIH Image).

EXAMPLE 4

Preparation of Ivory Slices

Elephant ivory (kindly obtained from Dr. B. Irrall, Bundesamt für Veterinärwesen, Berne Switzerland) was used as mineral substrate to assess osteoclast resorption activity. The ivory was cut into 4×4×0.1 mm slices with a Isomet low-speed saw (Buehler Instrument, Evanston, Ill.). Resulting slices were cleaned by ultrasound for 30 sec in de-ionized water. Thereafter the pieces were air-dried, gas sterilized and subsequently degassed under vacuum for 24 h.

EXAMPLE 5

Effect of Beta Glucan on Bone Resorption Through Osteoblast as Assessory Cells

Based on the fact that the osteoclast suspension used to assay bone resorption in vitro, is contaminated with other cell types noticeably with osteoblasts, made it necessary to examine whether osteoblasts act as accessory cells in the beta glucan effect on osteoclastic resorption.

Fully functionally clonal osteoblastic CRP10/30 and clonal preosteoblastic CRP5/4 cells were cultured with and without different concentrations of "beta-G" in the presence of 2% FBS. After 5 hours incubation, media were replaced and the cells were cultured for an additional 24 hours in the absence of the test substances. The conditioned media were collected and concentrated to 1/10 of its volume using an ultrafiltration device equipped with a filter with a molecular cutoff of 1 k. The concentrated conditioned media were reconstituted to their original volumes with fresh culture medium an subsequently tested on isolated osteoclast as described above.

The results of scoring for the number of osteoclasts (TRAP+ multinucleated cells) and resorption lacunae (pits) show that at concentrations of 100 pg there is an inhibition of pit formation that could not be observed in control cultures (nontreated osteoclasts). Increasing the concentration of beta glucan does not increase inhibition of osteoclast activity; in fact, actually a reduction of the inhibition was measured. (FIG. 1). At 100 pg the effect is similar to the effect obtained with a biphosphonate; bisphosphonates are used in various forms as drugs to control osteoporosis.

An inhibition of the number of resorption pits can result from an inhibitory effect upon osteoclast resorption activity (pits formed/osteoclast, from inhibition of the number of osteoclasts recruited from precursor cells, or a combination of both. In an analysis of osteoclast recruitment, extremely low concentrations of beta glucan decreases the number of osteoclasts formed (FIG. 2). At concentrations as low as 100 pg there is a decrease of 30%, and at concentrations of 1 ng and 10 ng there is an inhibition of approximately 50%. Increasing the concentration of beta glucan does not increase inhibition of osteoclast formation, but rather the effect diminishes. This observation is consistent with the fact that beta glucan has its effect via a receptor and that high concentrations lead to receptor down regulation. In addition, based on the ratio of pits/osteoclast (resorption activity) and the average resorption (areas/pit of treated and control cultures), it is concluded that beta glucan inhibits the recruitment of osteoclasts rather than the resorption activity.

In osteoporosis, which affects mostly older individuals and particularly post-menopausal women, combined with increased bone resorption there is a slow-down in bone formation by osteoblasts, which occurs normally due to the aging process. Beta glucan moderately enhances differentiation and osteoblast formation, thus supporting bone formation.

Other beta glucans (prepared from different sources) also generate anti-resorptive activity. In FIG. 3 it is evident that the insoluble yeast beta glucan (Nayad), a beta glucan isolated from the mushroom blazei agaricus also inhibits pit formation. The inhibition appears to be the result of inhibition of osteoclast formation. FIG. 4 shows that in all beta glucans examined (yeast) soluble and insoluble (Nayad), beta glucan from *Blazei agaricus, Yunzhi* beta glucan and even Zymosan, which is a hot alcoholic extract of yeast with immuno-modulating activity, due to the beta glucan in Zymosan) are capable of inhibiting the formation of osteoclasts.

Both FIG. 3 and FIG. 4 show that the most potent inhibitor is the soluble yeast beta glucan.

Figure 5:
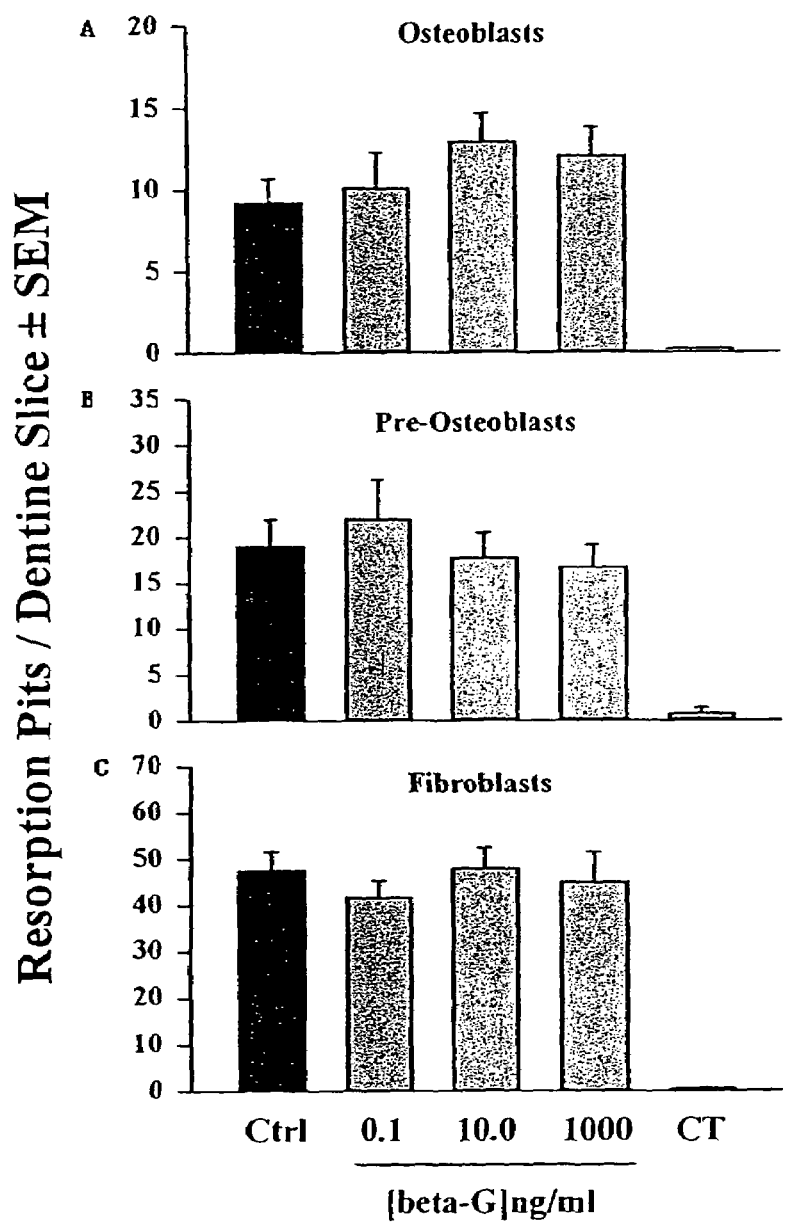
FIGS. 5 A-C is a series of graphs showing the effect of media conditioned by beta glucan-treated osteoblasts and fibroblasts on formation of osteoclastic resorption pits in vitro.

Beta glucan also modulates the development of osteoblasts. Clonal osteoblastic CRP10/30 cells, which are mature functional osteoblasts, and clonal osteoblastic CRP5/4 cells, which are immature osteoblasts, were cultured in the presence of soluble beta glucan prepared as described herein. When the cells reached confluence, alkaline phosphatase was measured in the two types of cells. FIG. 5 shows that the alkaline phosphatase of the mature osteoblastic cells was not affected; whereas the alkaline phosphatase in the immature osteoblastic cell increased (FIG. 6), indicating that beta glucan stimulates the development of immature osteoblastic cells (CRP5/4) to mature osteoblasts.

Although the invention has been described with reference to the presently preferred embodiment, it should be understood that various modifications can be made without departing from the spirit of the invention. Accordingly, the invention is limited only by the following claims.

What is claimed is:

1. A method for purifying previously isolated soluble beta-1,3/1,6-D-glucan of low molecular weight, comprising:
    a) suspending dry weight beta-1,3/1,6-D-glucan in a first volume of water and an effective amount of carbohydrase enzymes while heating at 10-80° C. and stirring;
    b) collecting beta-1,3/1,6-D-glucan and pumping it through a first filter forming an ultrafiltrate;
    c) dialyzing the ultrafiltrate by pumping the ultrafiltrate through dialysis fibers with a molecular weight cut-off of about 1500 daltons;
    d) concentrating the ultrafiltrate in alcohol; and
    e) purifying the ultrafiltrate, thereby purifying soluble beta-1,3/1,6-D-glucan having a molecular weight of about 12,000 to 60,000 daltons and containing about 4% protein and >10% $\beta(1\rightarrow6)$ bonds.

2. The method of claim 1, wherein the beta-1,3/1,6-D-glucan is from fungi or bacteria.

3. The method of claim 2, wherein the fungi is one or more yeast.

4. The method of claim 1, wherein the beta-1,3/1,6-D-glucan is obtained from bacteria.

5. The method of claim 1, wherein the first water volume is about 3 volumes.

6. The method of claim 1, further comprising suspending the beta-1,3/1,6-D-glucan in a second volume of water.

7. The method of claim 5, wherein the second volume is about 20 to 25 volumes of water.

8. The method of claim 1, wherein the heating is a temperature about 40° C.

9. The method of claim 1, wherein the carbohydrase is L beta-1,3-glucanase.

10. The method of claim 9, wherein the L beta-1,3-glucanase is viscozyme.

11. The method of claim 1, wherein the heating is a temperature about 80° C.

12. The method of claim 1, wherein the first filter collects ultrafiltrate of about 100,000 Daltons or less.

13. The method of claim 1, wherein the collecting lasts about 10 hours.

14. The method of claim 1, further comprising a monitoring step after the collecting.

15. The method of claim 13, wherein the monitoring comprises checking the ultrafiltrate for reducing sugars.

16. The method of claim 15, wherein the monitoring is every volume of ultrafiltrate collected.

17. The method of claim 16, wherein the volume is every liter.

18. The method of claim 1, wherein the collecting further comprises further collecting of the ultrafiltrate using a second filter.

19. The method of claim 12, wherein the collecting further comprises further collecting of the ultrafiltrate using a second filter.

20. The method of claim 18, wherein the second filter collects ultrafiltrate of about 1500 Daltons or less.

21. The method of claim 19, wherein the second filter collects ultrafiltrate of about 1500 Daltons or less.

22. The method of claim 1, wherein the dialyzing is at a rate of about 800 mL/min.

23. The method of claim 1, wherein the concentrating comprises reverse osmosis.

24. The method of claim 23, wherein the concentrating further comprises precipitating in ethanol.

* * * * *